United States Patent [19]

Bergstrom et al.

[11] Patent Number: 4,630,481
[45] Date of Patent: Dec. 23, 1986

[54] METHOD AND INSTRUMENT TO ESTIMATE THE WEIGHTS OF GREEN TREES AND LOGS

[75] Inventors: Gary C. Bergstrom, Jacksonville; Michael B. Lambert, Boring, both of Oreg.

[73] Assignee: The United States of America as represented by the Secretary of Agriculture, Washington, D.C.

[21] Appl. No.: 764,040

[22] Filed: Aug. 9, 1985

[51] Int. Cl.[4] .............................................. G01G 5/02
[52] U.S. Cl. ........................................ 73/437; 73/450
[58] Field of Search .................... 73/437, 450; 177/207

[56] References Cited

U.S. PATENT DOCUMENTS

| | | | |
|---|---|---|---|
| 171,670 | 1/1876 | King | 177/207 |
| 748,838 | 1/1904 | Broestler | 73/450 |
| 2,006,549 | 7/1935 | Hartley | 73/450 |

OTHER PUBLICATIONS

Schmidt, Ron E., A Method for Determining the Moisture Content and Specific Gravity of Wood Chips in a Pressurized Water System, Apr. 1968.

Primary Examiner—Stephen A. Kreitman
Assistant Examiner—Scott M. Oldham
Attorney, Agent, or Firm—M. Howard Silverstein; David G. McConnell

[57] ABSTRACT

Method and apparatus to estimate the weight of the trees and logs in a stand of trees before harvesting to maximize the efficiency of aerial logging are disclosed. A hydrometer that has a chamber which accepts a small known volume core from the tree determines the density thereof. Statistical modeling permits weight estimations for the entire stand based on this density and other conventional information about the stand of trees.

13 Claims, 9 Drawing Figures

FIG. 6
CURVES SHOWING PERCENTAGE OF SAPWOOD $$SAPWOOD (\%) = \frac{4(IOS)(DIB-IOS)}{(DIB)^2} (100)$$

FIG. 7
DIAMETER RATIO FUNCTION (OUTSIDE BARK)

$$R_{DOB} = 1 - 1.879*RH + 7.003*RH^2 - 15.361*RH^3 + 15.323*RH^4 - 6.086*RH^5$$

FIG. 8
DIAMETER RATIO FUNCTION
(INSIDE BARK)

$R_{DIB} = 1 - 1.449*RH + 5.442*RH^2 - 12.996*RH^3 + 13.759*RH^4 - 5.753*RH^5$

FIG. 9
GREEN DENSITY FUNCTION $GREEN\ WOOD\ DENSITY = 47.713 - 39.089*RH + 73.448*RH^2 - 39.65*RH^3$

METHOD AND INSTRUMENT TO ESTIMATE THE WEIGHTS OF GREEN TREES AND LOGS

FIELD OF INVENTION

This invention pertains to an instrument for measuing density and particularly to such an instrument useful to measure the density of green wood. The instrument is known as a xylodensimeter. The invention also pertains to a method for estimating the weight of large numbers of trees using curves generated by the instrument and a first set of techniques, and then a second set of techniques to use the curves and data generated by the instrument to determine the weight of the logs and the boles in the stand of trees.

BACKGROUND OF THE INVENTION

In the last twenty years or so, there has been a growing emphasis in the forestry business on developing logging systems which depend upon air lifting of the logs out of the cutting area. These logging systems depend primarily on helicopters, designed to lift heavy loads, and also upon balloons and airships. Such aerial systems increase the efficiency of the lumbering operations through larger lift capacities, improved access to remote timber which perhaps could be reached in no other way, and reduced construction costs for roads for trucks. The expense of trucking is also substantially reduced. The "bottom-line" result is lower primary transportation cost per unit volume of timber. Another very important advantage is that the overall impact on the envionrment is greatly reduced.

However, such aerial systems, for maximum efficiency, require accurate estimates of the trees to be harvested. These estimates include sizes of the trees, weights of the logs, and total weight of the stand of timber to be harvested. If these estimates are wrong to a significant extent, various problems result. It may be found that the helicopter cannot lift a particular log at all. On the other hand, if the logs are cut too small, then the helicopters will be underloaded, and this will result in extra flying time, which reduces efficiency and increases costs. Further, depending upon the total weight of harvested trees to be removed, and their distribution as to sizes, both lengths and diameters, the managers can select the particular type of equipment and schedule the number of manhours to closely match the requirements of the work, thus eliminating any wasted time, and using the most efficient logging and airlifting capabilities for the particular project requirements.

Although the forest industry has recognized the above considerations since the early 1960's, when heavy lift aerial logging came into use, methods and apparatus to generate accurate estimates of green log weights has received little attention, prior to the present invention.

Generally, in order to provide an accurate estimate for a single tree, the two important variables are the volume and green density of the entire bole. Green density is considered as the dry density of the wood plus the moisture plus the weight of the bark. Put another way, green weight is simply the weight of the freshly cut bole.

PRIOR ART DENSITY MEASUREMENT

The prior art depends primarily on a system known as the wood disc technique for measuring the density of green lumber. This system is well known to those skilled in the art. It basically comprises cutting down the tree, cutting a plurality of discs at various heights along the bole, and then performing fairly sophisticated laboratory techniques dealing with the moisture, the heartwood and the sapwood of the samples to come up with numerical values of the density for that particular tree. This prior art technique has a large number of rather serious disadvantages in and of itself and especially as compared to the advantages of the present invention.

This prior art system involves destruction of the particular bole being measured. Measurements cannot be performed in the field since they require laboratory equipment, including critical temperature measurements, ovens for drying moisture out of the wood, and the like. The cutting of the discs requires more skill than the average forest worker possesses as the discs must be accurately cut. The discs must be marked so that their position on the tree can be determined.

SUMMARY OF THE INVENTION

The invention method and instrument are highly adaptable for field use, are relatively inexpensive, permit generation of meaningful estimates in the field on a "real time" basis, require only basic forestry skills, and require use in the field of only the invention instrument and a programmable calculator or perhaps a small computer as opposed to much more sophisticated computing equipment.

The invention permits the production of very accurate estimates of green bole weight for timber ranging from a single tree to very large stands of trees in a relatively rapid period of time, in the field.

The invention method incorporates the use of certain tables of data and/or curves of such data, which once generated for a particular species of commercial timber can be reused for similar stands of that kind of wood. This produces even greater advantages for the present invention, since commercial timber is limited to a relatively small number of species. Having such curves and/or data tables available, even further simplifies the application of the invention method to weight estimation of a stand of such trees.

In summary of the method of the invention, it is a kind of modeling technique dependent upon the data generated by the instrument of the invention, which when applied to large stands of trees gives highly accurate weight estimates of all of the trees in the entire stand.

The instrument of the invention is in the nature of a hydrometer to measure cores of wood taken from sample trees at selected intervals along the length of the bole transverse to the axis of the tree. A scale using the teachings of the invention is provided to make a determination of the percent sapwood and percent heartwood in the cores in order to accurately apply the method of the invention to estimate the weight of a single tree as well as the weight of an entire stand of such trees.

The instrument portion of invention also includes a combination float chamber and storage chamber which provides additional advantages in and of itself to the invention measuing instrument particularly adapted for rugged field use as is anticipated in forestry operations. The two tubes, float chamber and storage chamber, are identical, and are joined together along their length by suitable adhesives or other joining means. The float chamber has a predetermined quantity of water therein and is provided with water-tight sealing means, and the companion chamber is provided with a spring and shock absorbing means to safely store the instrument when it is not in use.

The invention instrument has another advantage in that it is extremely not critical in regard to the amount of water used to float the invention device. The results are read out at the minicus of the water where it intersects the quill of the instrument, and so long as there is sufficient water to float the sample chamber and quill assembly, it does not matter how much or how little water is in the float chamber.

The storage chamber includes shock absorbing means at the inner end and a shock absorbing elastic material mounted in the cap at the opposite end, the dimensions being such as to hold the relatively delicate quill and sample chamber assembly immovable in the storage chamber when the quill and storage chamber assembly is not in use. In this manner, users have the instrument completely ready for use by simply removing the two plugs closing off the float chamber and the storage chamber, to thereby render the instrument immediately ready for use. One need only insert a core to be measured into the sample chamber.

The combination core chamber and quill assembly is of relatively simple construction, fabricated of rugged materials, and lends itself to the demands of the use to which it is put.

The instrument of the invention includes a scale and the method dictates its manner of use in such a manner as to produce cores of standard lengths with appropriate ratios of sapwood and heartwood so as to permit accurate use of the invention method based on the instrument. This scale requires no particular skill to use, and the only additional tool required is a sharp knife for cutting the cores to accurate lengths.

The cores are made using coring tools well known to those skilled in the art and which are well established.

The invention uses a reversal of the normal technology of hydrometers. In normal use, the specific gravity of a liquid of unknown specific gravity is determined based on its ability to float materials of known density. In the present invention, water, which of course is of known specific gravity, is used to float the sample chamber with the sample therein, and the quill yields data concerning the specific gravity or density of the sample. This system has previously been calibrated to be neutral for the sample chamber and quill assembly with only air inside the sample chamber.

ADVANTAGES OF THE INVENTION

The invention provides a relatively simple means to determine the accurate percentage of sapwood in each core sample and thus, in each sampling location on the bole, or on the living tree.

The invention utilizes a well-proven hydrometer principle, but does so in reverse, to measure the density of green wood.

Because the invention works in the field and on site and in a real-time mode, numerous advantages are produced. The density of the green wood is measured while it is still alive or freshly cut. Deterioration with time, loss of moisture and the like is completely avoided. The invention method and apparatus can be applied to stands of timber that have had no prior measurements of weight or density. Workers having no more than ordinary forestry skills are needed to use the estimation system utilizing the invention. The skill of the workers and their prior experience in similar timber conditions is irrelevant to the accuracy of the results produced. The actual form and geometric shape of the trees measured on-site is utilized.

The statistical and mathematical techniques of the invention employ high order linear functions for density and diameter with respect to relative tree height and relative log length to produce readily utilizable tables of data and equations. These can be implemented using simple computers or even hand-held programmable calculators.

The final weight estimates are produced on-site and in real time as the work is progressing.

The tables or curves generated from one stand of trees can be applied to a similar stand of trees, thus saving some of the surveying and inventory work as well as the numerous density measurements that went into producing the first set of tables and curves.

The invention mathematical analysis system, once brought into creation, permits optimization, based on any criteria useful to the user. For example, the best possible combination of logs based on financial return could be produced. The cutting of the logs can be determined in accordance with the equipment available to move the logs. Waste of trees and/or logs can be minimized or even eliminated. The invention permits maximization of financial return, maximum utilization of equipment available, and maximization of finished lumber produced after the logs are further processed.

ADVANTAGES WITH RESPECT TO THE PRIOR ART

An average density of the wood has been assigned based on hand-book values, experience, or measurements made after the harvest. Volumes are estimated, based on the assumption that the tree will fit some standard form, again arrived at by experience of the estimator, or measurements made after the harvest. When dealing with aerial logging techniques, the errors is introduced by these unscientific prior art methods are simply unacceptably large, the result is that the aeial operations become unprofitable, and in some cases, impossible to perform.

Many methods are available in the prior art for measuring the density of green wood. The disc method is destructive and introduces unacceptable delays. The truck weighing method occurs after the harvest and is very inaccurate. Nuclear densitometers are extremely expensive instruments and are unacceptably cumbersome for field use.

The invention distinguishes from the disc method of density measurements, in that it is nondestructive and requires no laboratory work. The invention system can be done in real time, and a portable, rugged instrument for field use is provided.

The invention distinguishes over the truck weighing method in that the invention is sensitive to species, tree size, tree shape, location of the log within the bole, and the like. Also, the invention can be applied to living trees.

The invention has advantages over the nuclear densitometer in that it is considerably less expensive, is not subject to regulation, is not subject to the hazards inherent in nuclear materials, and it corrects for the actual proportion of heartwood and sapwood. Heartwood and sapwood have markedly different densities, and this correction is essential for producing accurate estimates of bole and log weights.

As to volume measurements, the forestry industry, since it is concerned primarily with finished lumber, has many techniques that depend upon or produce results in board-feet. Such techniques are immaterial for estimating weights of green logs with bark for aerial logging. Thus, all such prior art finished lumber estimating techniques are inapplicable to the invention's environment.

Another advantage of the invention is that once the tree has been integrated using the mathematical techniques of the invention, the actual center of gravity of the tree or bole or bole segment (log) may be calculated. This information can be very important as to the directional felling of the trees and the handling of extremely large and heavy logs and trees. This results in substantial improvements in the areas of safety and recovery of useable lumber from the trees.

Thus, there is provided a method and apparatus well suited to the demands of its use, which provides important advantages over the prior art in this area, which is relatively inexpensive to manufacture, which is easy to apply, using only basic forestry skills and no other forestry skills, which produces tables of data and/or curves which can be applied to other stands of similars sorts of timber, and which is generally highly advantageous and efficient in the demands of practical use.

BRIEF DESCRIPTION OF THE DRAWINGS

The invention will be described below in detail with reference to the accompanying drawing also forming a part of this disclosure in which.

DETAILED DESCRIPTION OF THE PREFERRED EMBODIMENT

It is anticipated that a normal application of the method and instrument of the present invention will be in planning for the harvesting of timber on a commercial scale. The person doing the planning needs to know how much total weight of timber is in a particular stand planned to be harvested and needs to know how much the individual logs will weigh. This information is needed in order to plan the number of manhours required to harvest the timber. It is also needed in order to allocate the types and sizes of equipment needed to handle the logs. If the equipment available is limited, the weight estimates produced by the invention will help decide the lengths to which the logs will be cut so that the equipment available will be able to handle such logs.

This kind of consideration is highly critical in certain logging operations, particularly aerial logging operations, wherein helicopters are used. Overloads in helicopter logging are dangerous and can produce impossible situations, that is the helicopter simply cannot lift the log. Such overloads are extremely costly in lost time, having to do work over again, and often results in loss of otherwise merchantable timber.

The estimates produced by the present invention for aerial logging prevents underloads. That is, where the logs are cut considerably too light for the ability of the helicopters. Such underloads result in very severe cost penalties resulting from excess round trips made by the helicopters and the like. Finally, where the logger does not own the property involved, as in logging operations on government-owned forest lands, such weight information in advance could help a logger decide on whether or not he wants to make a bid on the particular stand of timber at all. That is, the nature of the logs may be such that it is not economical for this particular logger, in view of the sizes and types of equipment which is available to him, to take that paticular job because the logs produced would be either too small or too large which would, in either case, result in uneconomical operation for that particular logger with his particular set of equipment available.

The present invention comprises an instrument having two versions, shown in FIGS. 1-5, and includes a method dependent upon this instrument. Curves useful in this method are shown in FIGS. 6-9.

The invention instrument is in the nature of a hydrometer useful for measuring the specific gravity of materials. It works on a kind of reverse principle. That is, hydrometers such as are typically used to determine the freezing temperature of fluids used in automotive radiators, use solid materials of known density to determine the specific gravity and thus the freezing point of liquids of unknown density. The present invention utilizes a liquid of known density, preferably water, to determine the specific gravity and density of a solid material which is floated in a sample chamber in the water. The chamber and quill assembly are previously calibrated to float at a neutral or reference point in the water when there is no sample to be measured in the sample chamber.

Figures 1, 3:
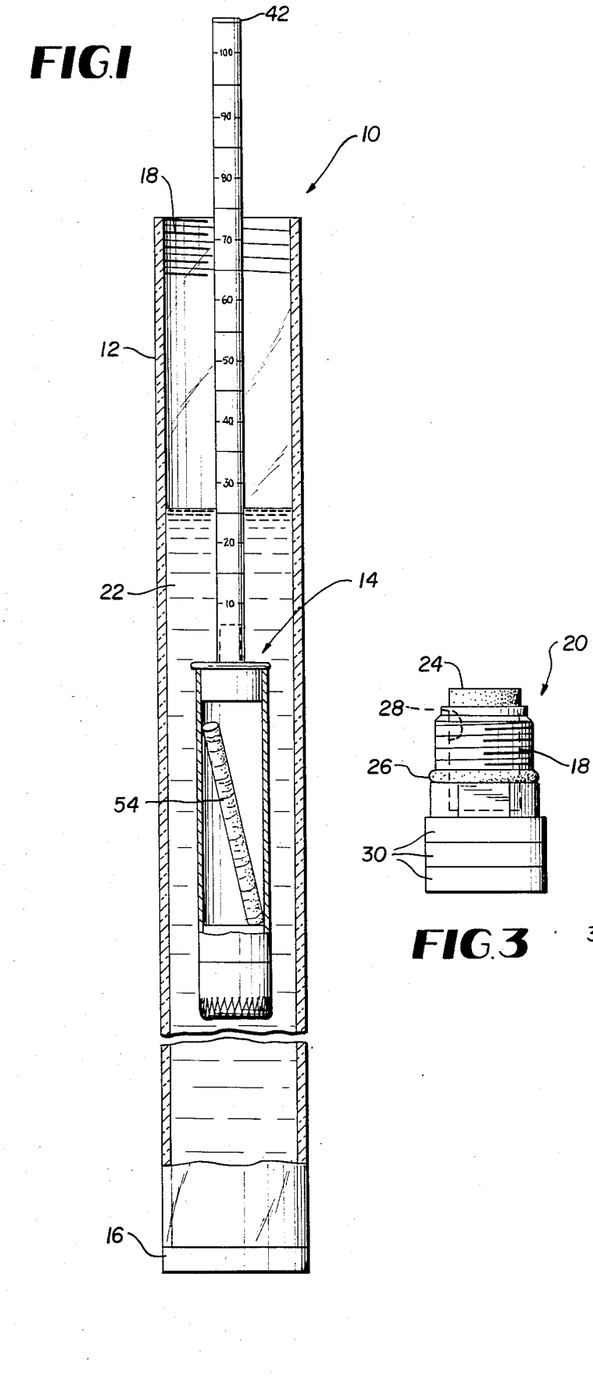
FIG. 1 is a vertical elevational view, partly in section and partly schematic, showing the instrument of the invention.
FIG. 3 is a vertical elevational view of a cap used for the floation tube of FIG. 1 as well as for the storage tube and float tube combination of FIG. 5.

Referring to FIG. 1, this embodiment of the invention comprises an instrument 10 made up of a flotation chamber 12 and a quill and sample chamber assembly 14. Float chamber 12 is preferably made of tubular acrylic, a clear plastic, sealed at its lower end by an end cap 16 and formed with threads 18 for cooperation with a water-tight sealing plug 20, shown in FIG. 3. Chamber 12 is provided with a quantity of water 22 to a arbitrary level therein. The end cap 16 is secured in place as by glueing, heat sealing, or the like dependent upon the particular plastic used in the fabrication. It is important that the tube 12 have good optical qualities and allow the markings on the quill assembly 14 to be read through the wall of the tube 12.

Because of the reverse hydrometer principle of operation of the instrument 10 as described above, the length of the flotation chamber, as well as the amount of water therein, are both not critical parameters. This facet of the invention facilitates manufacture and facilitates use in the field which are both very important advantages for the present invention.

The criteria that are considered include that the tube 12 be sufficiently long as to float the assembly 14 therein, in such a manner that a full scale of the quill, from 0–100, be readable on the meniscus of the water, and that sufficient water be in the tube that the assembly can sink up to the maximum mark (100), while the chamber still floats and does not strike the bottom sealing end 16.

The plug 20 of FIG. 3 is shown as including a member 24 formed of soft resiliant material, the purpose of which will be described below in regard to FIG. 5. The plug 20 includes male threads 18 thereon, and an "O" ring 26 to form a fluid-tight seal, together with the female threads 18 at the top of the tube 12. This permits the predetermined amount of water, preferably distilled water, to be held sealed in the chamber 12 between periods of use. During the experimental and development work on the invention, a quantity of water 22 has been reserved for many months and through many uses, again yielding important advantages to users who must cope with the rugged conditions of logging field use. The elastic material 24 is readily removable from the cavity 28 formed in the end of the plug 20 for a reason which will appear below. For ease of handling, a series of discs 30 are secured together and to the end of the plug 20 to serve as a handle in use. The top annular surface of the tube 12 has a smooth finish, and may even be tapered slightly, in order to cooperate with the "O" ring 26 to form a watertight seal.

Figure 2:
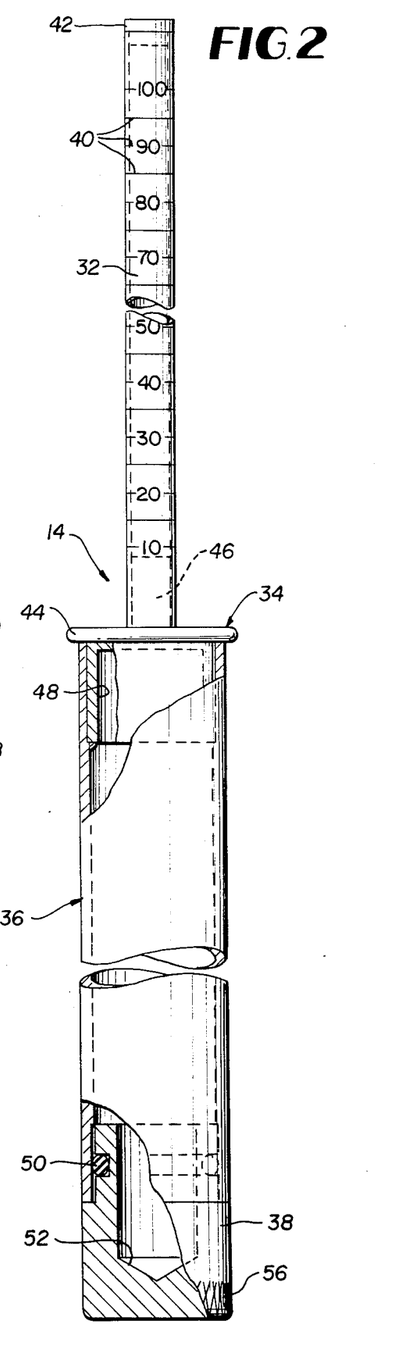
FIG. 2 is a similar vertical elevational view of the sample chamber and quill assembly shown in FIG. 1.

Referring to FIG. 2, the quill and sample chamber assembly 14 is made up of a quill 32, a quill adapter 34, a sample chamber 36, and a sample chamber plug 38.

The following specific descriptions are taken from a prototype of the invention which has been built and which successfully demonstrate the applicability of the invention instrument and the viability of the invention method. The quill was machined from a length of X7-1614 Easton aluminum arrow shafting. This material has the advantage of being manufactured to close tolerances, thus eliminating any machining of its diameter. The arrow shafting has an anodizing finish and is available in different colors. The preferred embodiment was black, and the numbering and lines 40 on the quill were created by engraving so that easy-to-read bright aluminum color indicia were created on the black background on the arrow shafting. The top of the quill is sealed off by a plug 42 to protect the end of the quill when it is stored and to prevent accidental entry of water or other material into the quill.

The quill adapter 34 serves to join the quill 32 to the sample chamber 36 in a permanent manner, and also is provided with an edge 44 on a slightly enlarged upper main plate to keep the assembly 14 floating freely with respect to the inside surface of the tube 12. That is, as the assembly 14 moves in use, the contact is between the inside of the tube 12 and the edge 44, thus substantially eliminating the possibility of the assembly 14 "hanging up" in the tube. This edge 44 is preferably chamfered and polished in order to facilitate its motion with respect to the inside of the tube. The adapter 34 further includes a pin portion 46 at the upper end which fits inside the quill 32 and which is secured by any suitable means, such as, adhesives, crimping, or the like. The lower end of the adapter 34 is formed with a tubular portion 48 which is likewise secured to the upper end of the sample chamber 36.

The sample chamber 36 is simply a predetermined length of aluminum tubing having its inside surface finished at both ends, the one end to cooperate with the tubular portion 48 of the quill adapter 34, and the other end to cooperate with the "O" ring 50 on the sample chamber plug 38.

The plug 38 serves a surprising number of purposes. Most obviously, it permits rapid sealing and unsealing of the sample chamber 36 in order to remove and insert samples whose specific gravity is to be measured, see the sample 54 therein, in FIG. 1. Sample 54 is a core of green wood as is useful in the method of the invention, described in more detail below.

Returning to plug 38, this member is formed from a solid block of aluminum, and in addition to acting as a removable seal, also acts as a counterweight to hold the assembly 14 floating upright. It is also provided with a machined opening, preferably simply a drilled hole 52, to permit a final trim adjustment or calibration of the assembly 14 during manufacture. The outside surface of the plug 38 should closely match that of the sample chamber 36, to a smooth and to prevent sticking of the assembly 14 in the tube 12 during use. The end of the plug 38 may be knurled as at 56 to facilitate manually handling its sliding in and out of the mating surface at the bottom of the sample chamber 36. Further, waterproof silicone grease can also be provided at that interface to prolonge the life of the "O" ring 50 and to facilitate use.

In regard to calibration using the drilled hole 52, as the last step in manufacture, this hole is repeatedly drilled deeper and deeper until the assembly, empty of anything other than air inside the sample chamber 36, will float in water with the zero indicia on the quill 30 at the meniscus of the quill in the water. After the assembly 14 is calibrated to float empty at the zero indicia, the spacing of the remaining indicia can be determined by inserting a volume of known weight or density into the sample chamber 36 and floating the assembly 14 in water in the tube 12. The quill 32 can then be marked where it crosses the meniscus for the known weight or density. Then, the other indicia can be proportioned appropriately.

Figure 4:
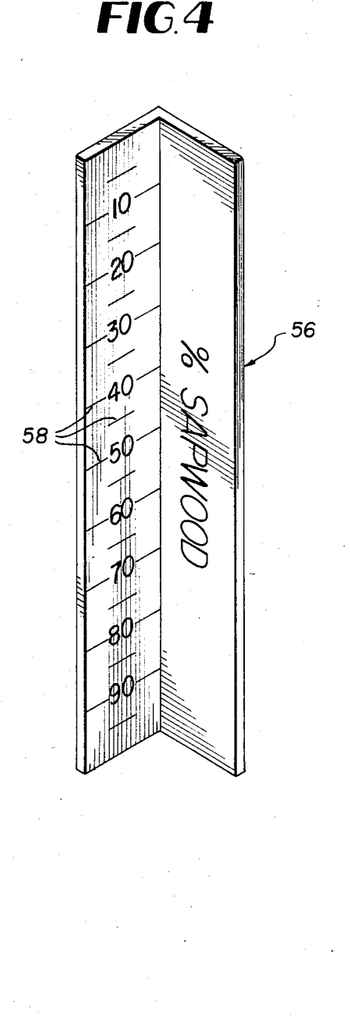
FIG. 4 is a perspective view of the scale used in the invention method for preparing core samples for use in the instrument of the invention.

FIG. 4 shows a scale 56, which is a simple length of "L" shaped aluminum to a predetermined length and bearing indicia 58 thereon. The indicia 40 on the quill and the indicia 58 on the scale are dictated by the requirements of the method of the invention, and their use and applicability will be explained in more detail below in regard to the method.

Figure 5:
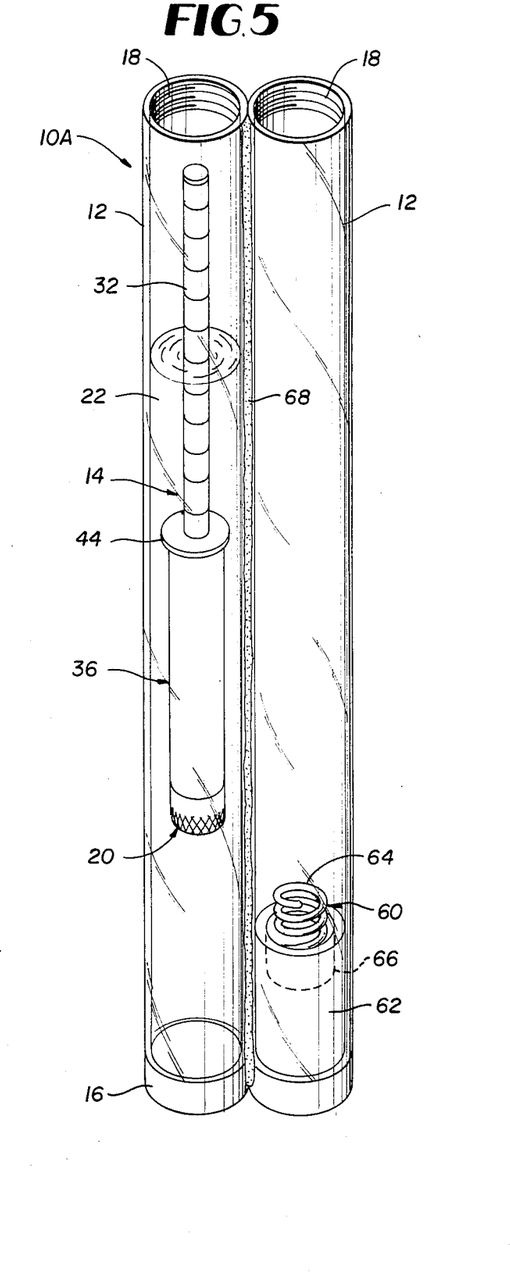
FIG. 5 is a vertical perspective view of another embodiment of the invention showing a combination storage chamber and flotation chamber, and also showing the manner of use of the invention instrument.

FIG. 5 shows an embodiment of the invention highly suited to rugged logging field use. This is made up of the quill and sample chamber assembly 14 identical to that shown in the preceeding Figures and described above. The FIG. 5 instrument 10A, includes two identical tubes 12, one of which is provided with the quantity of water 22, and the other kept dry. The dry tube, called the storage chamber, is fitted with a spring protective assembly 60 made up of a plug 62, having a recess in its upper end for acceptance of a coil spring 64, which has its outer end turned over and its inner end fitted into a chamber 66 machined into one end of the plug 62. Referring back to FIG. 3, the assembly 5 will include two of the plugs 20. The one which goes in the storage chamber tube 12 will include the elastic plug 24, and the companion plug for the water chamber, preferably, would not include that elastic material. The water would soak into the elastic shock absorbing material and be inconvenient to handle. However, if suitable materials were used, the two plugs 20 for the two tubes 12 of FIG. 5 could be identical. The two tubes 12 are joined together in a side-by-side relationship by adhesive 68, heatsealing, or the like to securely and permanently join the two tubes together.

The free length of the spring 64, with respect to the length of the plug 20 and the elastic material 24, is selected so that the assembly 14 will be fairly rigidly, but yet resiliently held between the material 24 and the upper end of the spring 64 when the plug 20 is screwed tightly down on the threads 18. This will prevent the quill and storage chamber assembly 14 from moving about as the assembly is transported. At the same time, the predetermined quantity of distilled water 22 can be held sealed in place by the companion plug 20 on the companion tube 12. This has proved to be, during testing of the invention, highly advantageous for rugged field use.

The instrument of FIGS. 1-5 has been developed for use with the invention method described below. However, this instrument has other utility. It is a basic scientific principle that a floating body will displace its own weight of the liquid in which it is floating. With the assembly 14 calibrated for the particular fluid, preferably water because of its easy availability, a sample in the chamber will produce a reading on the indicia on the quill at the meniscus proportional to the weight of the sample in the chamber. This is so because the assembly 14 has been previously calibrated, when empty, to float at the zero indicia on the quill. Thus, the indicia can be in terms of grams, ounces, or whatever is desired.

The present invention method depends upon producing cores of green wood of known volume. This is done by using a boring tool which produces a known diameter core, and using the scale 56 of FIG. 4 to produce a core sample of predetermined length. With diameter and length fixed, the core will then have a known volume. This invention instrument will produce its weight. Therefore, following the simple formula that weight is equal to density times volume, the remaining density parameter is easily produced. The indicia on the quill can then be in terms of density units, such as pounds per cubic foot or the like.

This same thinking can be provided to any kind of sample, it is simply necessary to produce samples of known volume and to calibrate the indicia for the particular liquid as well as for the anticipated weights of the sample to produce readings directly in units of density and/or weight of the sample in the floating chamber of assembly 14.

The invention also has versitility as to size. That is, the length of the sample chamber and assembly 14 as well as the length of the scale in FIG. 3 must match, and this length can be whatever is convenient for the particular purpose. For forestry operation core lengths in the range of 5-8 inches, with 6-7 inches being the most common, are anticipated. A sample core may be inserted into the sample chamber in pieces or sections, provided all parts of the sample core are included.

In applying the method and apparatus of the invention to use with a stand of timber concerning which no previous curves in accordance with the invention have been generated, the first step is a characterization of the trees in the stand. An important advantage of the invention is that once curves are generated for a particular kind of woods situation, those curves can be used again when the same environment is encountered again. For purposes of explanation, the procedure will be gone through including the generation of curves using the invention instrument, and then the use of these curves to get the necessary weight estimates will be explained.

The first step is the inventory or so-called timber cruise procedure. An experienced estimator will identify the mix of the species in the stand, the ages of the trees, the total number of trees, the height of the trees, the diameters of the trees, the aspect as to slope, and the like. This cruise or inventory is standard forestry procedure.

At the end of this inventory, the estimator will prepare a chart of the trees broken down into classes. This classification will depend upon the nature of the stand of trees. The more uniform the trees in the stand, the greater the accuracy of the weight estimates. However, if it is desired to more finely divide the classes in order to enhance the accuracy of the final estimates, then the time and cost for weight estimation will also increase. The estimator uses his skill in this classification, in order to make compromises in accordance with the usual and sound forestry procedures.

The invention has been used in experimental applications. Once such application included a stand of 175 trees. This was a commercial stand, the trees had been thinned, and the remaining trees to be harvested were all of one species, Douglas-fir, and had a distribution as a result of the inventory as follows:

TABLE 1

| Diameter at Breast Height (DBH) | | |
|---|---|---|
| DBH | Number | Samples |
| Up to 20" | 8 | 1 |
| Over 20" up to 30" | 93 | 10 |
| Over 30" up to 40" | 63 | 6 |
| Over 40" | 11 | 1 |
| | 175 | 18 |

TABLE 2

| Heights | Number |
|---|---|
| up to 99' | 1 |
| 100-111 | 2 |
| 112-123 | 3 |
| 124-135 | 2 |
| 136-147 | 38 |
| 148-159 | 45 |
| 100-171 | 42 |
| 172-183 | 28 |
| 184-195 | 6 |
| over 196 | 8 |
| | 175 |

The third column, marked "Samples" in TABLE 1, indicates the number of trees from each DBH category which was selected to prepare the curves which appear in the subsequent Figures and are described below in regard to the method.

The sampling was made on a roughly 10 percent basis to represent the entire stand. This particular stand was unusually uniform both as to containing essentially a single species, and as to age, size and diameters. In a mixed stand, or in a more rugged terrain, or the like, a larger sample might have to be taken to get statistically valid sampling or modeling of the entire stand. Such techniques are well known to those skilled in statistical analysis as well as in the appropriate forestry arts.

As the next step, the sample trees only are then cut down. This is usally not a serious problem since the stand of trees are soon to be harvested in any event. Further work can then be done on these boles, but the invention method can be applied, if necessary, to standing living trees.

The diameters inside and outside the bark at three-foot intervals along the entire merchantable length of the tree were then taken. These diameters were measured using tree calipers or a diameter tape, both common tools in forestry. The thickness of the bark was measured with a bark thickness gauge, or sometimes with a simple steel ruler. It was sometimes necessary to chop through the bark down to the sapwood. By substracting twice the thickness of the bark from the diameter outside the bark (DOB), it is possible to calculate the diameter of the solid wood in the tree, i.e., the diameter inside the bark (DIB). All of this data is collected in tabular form, or stored in computer or programmable calculator memory, depending upon the facilities available.

Simultaneously with the measurement of diameters at three-foot intervals, the boles were also measured as to the density of the green wood at regular intervals. For this particular experiment, six-foot intervals were used. A standard increment core borer was used to extract a wood core at the regular intervals. Each, core was examined to determine the thickness of the sapwood, inches of sapwood (IOS), this thickness was measured directly on the fresh core using a ruler, and the measurements were recorded.

Figure 6:
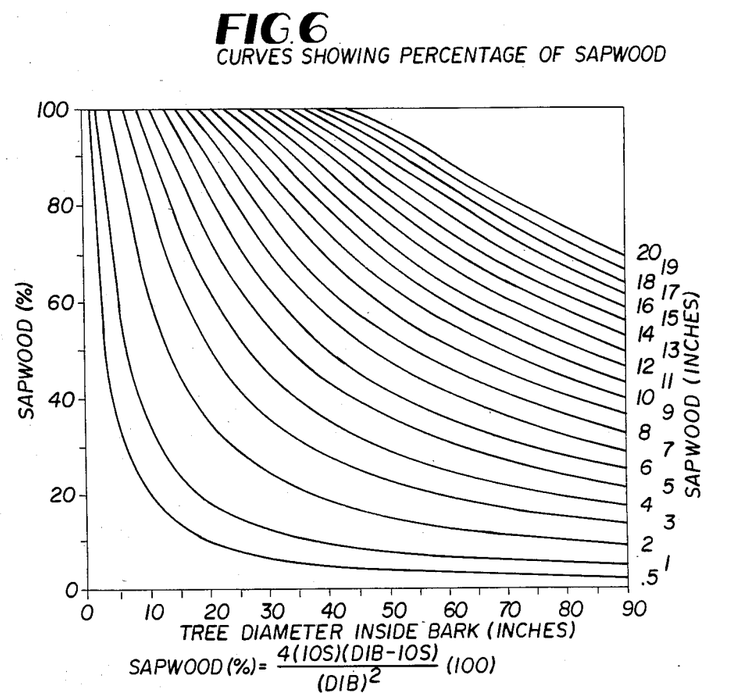
FIG. 6 shows a family of curves of data and the equation for generating the curves useful together with the scale of FIG. 4 of the method of the invention.

Knowing the diameter under the bark (DIB) and the inches of sapwood (IOS), the correct ratio of sapwood/heartwood can be calculated using a pocket calculator and the equation shown in FIG. 6, alternatively, or the curves shown in FIG. 6 can be used to determine the percent of sapwood in the tree at the height at which the core was taken.

With this data, that is the percent sapwood known, as set forth immediately above, the cores were then placed on the scale of FIG. 4 with the sapwood/heartwood transition, which is readily visible to skilled foresters and usually even to a lay person, at the appropriate point. This is, if the particular core had a 45 percent sapwood content, the core, which is considerably longer than the total length of the scale 56, was placed with the sapwood/heartwood transition at the 45 percent mark, and the core was then cut off at both ends so that its total length would be equal to the total length of the scale 56. As previously mentioned, the length of this scale corresponds to the capacity of the chamber 36 in the assembly 14 for any particular environment in which the invention method and apparatus is to be used.

Cores prepared in this manner now accurately represent the sapwood/heartwood ratio of the solid wood in the tree (excluding the bark) at the level or height on the tree at which the core was taken.

The thus prepared cores were then inserted into the chamber 36 of the assembly 14, the device floated in the water, and the density read off of the indicia at the meniscus of the water on the markings on the quill.

The invention method uses a relative height relationship rather than an absolute height relationship in order to increase the versatility of the statistical method of the invention. This relative height also permits the combining of density data from all of the sample trees within the particular tree class. Thus, tree height information was normalized to a relative height for each tree. For these purposes, relative height shall be understood to mean height with reference to a common base, such as the ground, the top of the stump, the breast height at which the diameter was taken, or some other consistent reference plane. All future heights then, are divided by the total height of that tree, with reference to the common base. For example, three feet up on a tree having a total height of 120 feet, is the same as a relative height of 0.0250, assuming an earth reference plane. However, if the tree is cut leaving a one-foot stump, then three feet up on the butt log will have a relative height equal to 0.0252, which is equal to three divided by 119, rather than 120, the one-foot correction being the allowance for the stump. In summary of this point, it can be seen that a relative height of 0.0 refers to the reference plane, a relative height of 1.0 means the height at the tip of the tree, and a relative height of 0.5 means half the height above the reference plane.

Figure 9:
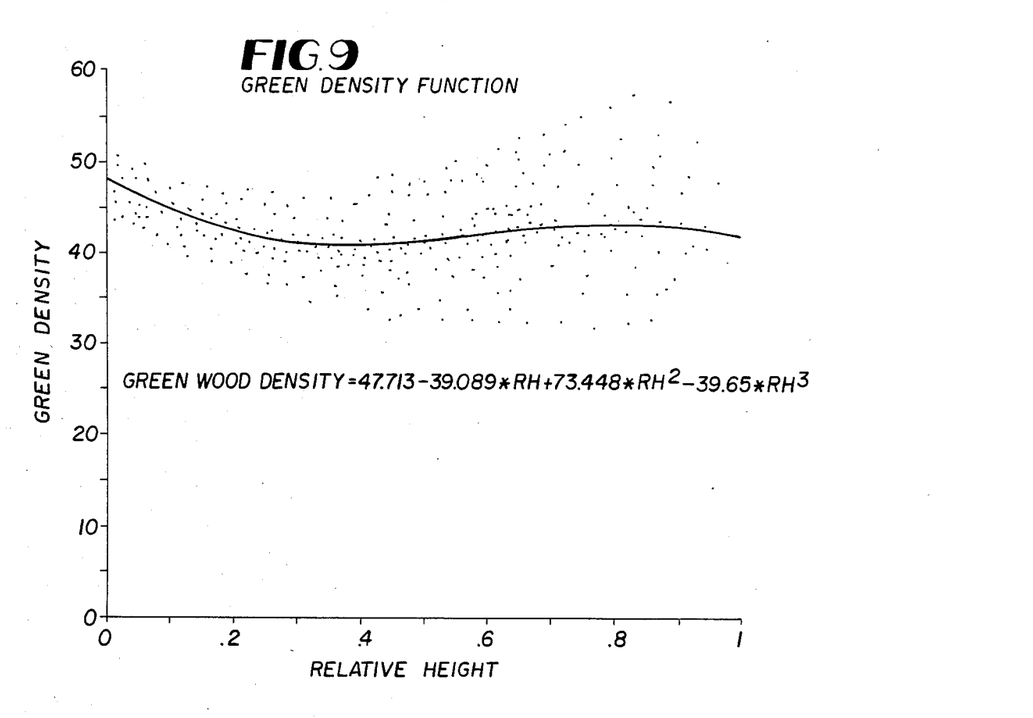

Referring back to the stand of 175 trees which was used in the experimental proving of the invention, Table 2 shows the actual height distribution of those trees. This was converted to relative heights, and the relative heights as compared to the green density measurements for the 18 sample trees at all of the planes at which cores were taken are shown in FIG. 9.

A smooth curve was drawn through all of the data points, this curve being fitted to the data by the method of least squares, a simple procedure using even only a programmable calculator. The equation shown in FIG. 9 for this curve is a polynomial derived by linear regression analysis. A standard statistical analysis software package was used for this work.

Using similar logic, in order to combine the diameter data for all of the sample trees, a relative diameter was used. This parameter, shown in FIG. 8 on the vertical axis, is simply the ratio of the actual diameter to the diameter at breast height. Thus, the DBH is the data plane in effect. For example, when the ratio is 1.0 the tree diameter is the DBH. At a ratio of 0.25, the diameter is one fourth of DBH, etc. The curve of FIG. 8 uses a regression analysis equation similar to that in FIG. 9, and all of the test data points are shown together with the curve which was fitted thereto using the least squares technique.

Figure 7:
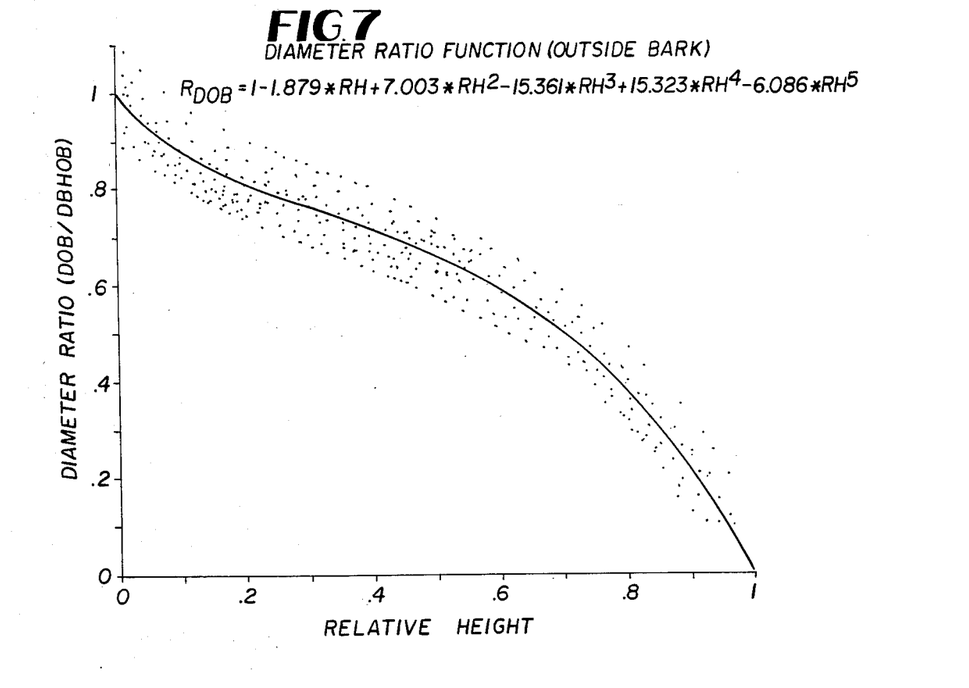
FIGS. 7, 8 and 9 are a set of curves of data produced using the instruments of FIGS. 1-4 or FIG. 5 in the method of the invention.
Figure 8:
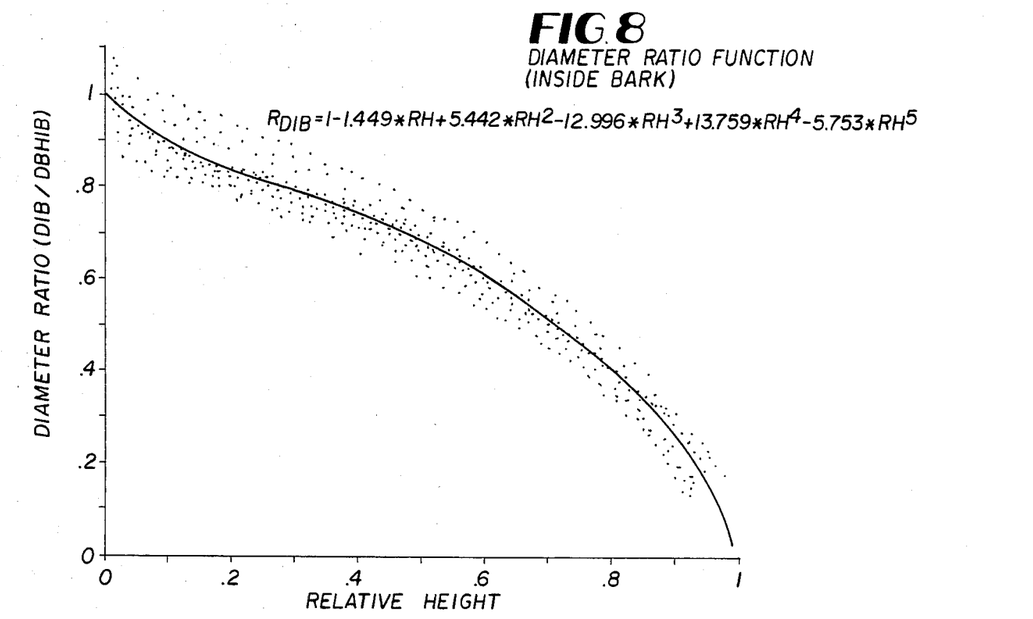

FIG. 7 shows a curve and an equation similar to that of FIG. 8 but related to diameter outside the bark.

At this juncture, the sample work (on the 18 trees in this case) is done and the curves of FIGS. 7, 8 and 9 have been brought into existence and are highly representative of the entire stand of timber from which the sample data was drawn.

If a similar stand of trees from which the curves of FIGS. 7, 8 and 9 were made should be encountered again, then these curves can be used again. Depending upon the criticality of the output estimates required, a more or less close "fit" of the data to the new stand of trees can be tolerated or not tolerated in deciding about reuse of these curves.

In summary of this point, if another like stand of trees are encountered, the curves can be used again.

Continuing now the description of the example involving the 175 trees, these curves, the data on which they are based, and a very simple computer or even a hand-carried programmable calculator, can be used to calculate incremental weight for very short lengths of any one or all of the trees in the stand. In this example, this was done by numerical integration of the density and diameter curves. For example, the weight of one tree at its relative heights between 10 and 10½ feet can be calculated. The product of density times volume is weight. The volume outside of the bark is calculated by using the curve of FIG. 7. This curve is entered at the relative heights for 10 and 10½ feet. The volume can then be calculated using an appropriate formula.

At this point, volumes for Douglas-fir butt segments were calculated by Bruce's (1982) butt log equation:

$$V = CL(0.25D^2 + 0.75d^2);$$

for western hemlock butt segments by the sub-neiloid rule, for midsegments of both species by the Smalian rule, for top segments of both species by the two-end conic rule (Dilworth 1981);

sub-neiloid rule:
$$V = CL \frac{(D + d)^2}{2};$$

Smalian rule:
$$V = Cl \frac{(D^2 + d^2)}{2};$$

two-end conic rule:
$$V = CL \frac{(d^2 + D^2 + Dd)}{3};$$

where:
V = volume of the log in cubic feet;
C = 0.005454 (unit conversion factor);
L = length of the log in feet;
D = average diameter outside bark for the large end of the log in inches; and
d = average diameter outside bark for the small end of the log in inches.

The reason for the need for different formulas is that the taper of trees typically varies continously throughout the tree over its height. These equations are well-known in these arts and give accurate values for volume for the crown, middle and butt sections of commercial quality boles.

Using the curve of FIG. 8, the volume of solid wood only is calculated. To this must be added the weight of the bark. The bark volume is the difference of the volume outside the bark less the volume of the solid wood inside of the bark. Once this volume is determined by a very simple calculation, weight is obtained by multiplying the volume times bark density. Values for bark density for different species are readily availble from handbooks and the like.

Returning to the example concerning a segment from 10 feet to 10½ feet, the volume inside the bark is multiplied by the green density at 10¼ feet. The value for green density is taken from the curve of FIG. 9. This manipulation gives the weight of solid wood for the tree section between 10 and 10½ feet. Total weight for the section is that weight plus the weight of the bark determined as set forth above.

In this manner, using a kind of an integration technique, the weight of the entire bole can be calculated. Again, using a relatively simple computer or even a sophisticated programmable hand-held calculator, these mathematical manipulations can be readily done. The curves, of course, can be stored as data in the memory of the calculating machine or computer being used, and actual curves on paper need not be brought into existence.

The classification of all of the trees in the stand into the TABLES 1 and 2 further simplifies and reduces the amount of calculations necessary. That is, the calculations can be performed on groups of trees of similar size, rather than on each tree of the entire stand individually.

Carrying the invention method another step, if the lengths of the desired logs are a controlling factor, or if the weights of the desired logs are a controlling factor, then the data can be manipulated as necessary to produce the appropriate estimates. That is, for example, the estimator may desire to know what the lengths of the logs will be if the weight of any one log is not to exceed a certain number of pounds. Conversely, if logs of a certain minimum length are required, then the data can be manipulated to yield estimates of the weights of such minimum length logs. Many other such approaches to the data produced in accordance with the invention will be clear to users familiar with the commercial demands of logging.

While the invention has been described in detail above, it is to be understood that this detailed description is by way of example only, and the protection granted is to be limited only within the spirit of the invention and the scope of the following claims.

We claim:

1. An instrument for determining the weight of a living or freshly cut tree, comprising a sample chamber and quill assembly, a float chamber to receive said sample chamber and quill assembly, a scale for preparing samples for use in said sample chamber and quill assembly, said samples comprising cores bored out of said living or freshly cut tree whose weight is to be determined and said cores being bored out of said tree transverse to the axis of said tree and at regular intervals along the length of the said tree and said cores being of a predetermined diameter, said scale comprising means to prepare said samples from said cores such that said samples will have a predetermined length so as to permit a sample so prepared to fit into said sample chamber and quill assembly and whereby a sample so prepared will have a predetermined volume, said scale comprising means to prepare said samples from said cores such that the ratio of heartwood to sapwood in said sample simulates that same ratio in the living or freshly cut tree at the height thereon at which the corresponding core was bored, and means to use the data produced by said instrument concerning all of said samples made from said cores bored at said regular intervals out of said tree to determine the weight of said tree.

2. The instrument of claim 1, and a predetermined amount of a predetermined liquid in said float chamber, means to selectively seal said sample chamber and quill assembly, indicia including a zero mark provided on said quill indicative of the weight of a sample sealed in said sample chamber when said sample chamber and quill assembly is floating in said liquid, and means to calibrate said sample chamber and quill assembly such that said sample chamber and quill assembly with nothing but air contained in said sample chamber will float in said liquid with said quill extending up out of said liquid and with the meniscus of said liquid on said quill occurring at said zero mark of said quill indicia.

3. The instrument of claim 1, said float chamber comprising transparent material whereby the meniscus reading of said liquid on said quill can be easily read through the wall of said float chamber.

4. The instrument of claim 2, wherein said predetermined liquid is water.

5. The instrument of claim 2, and means to selectively seal said predetermined amount of said predetermined liquid in said float chamber between used of said instrument, whereby said instrument is adapted to rugged field use.

6. The instrument of claim 1, wherein said float chamber and said sample chamber are both of tubular configuration, and an enlarged diameter rounded edge ridge portion formed on said sample chamber and quill assembly in a central region thereof to facilitate motion of said assembly in said liquid and in said float chamber.

7. A method of estimating how much a stand of trees will weigh after the trees are felled done while the trees are still standing, comprising the steps of:
1. classifying the trees in the stand according to at least their species, their heights, and their diameters, and recording the data produced thereby;
2. sampling all of the trees in the stand by statistically selecting numbers of sample trees based on the classification of step 1;
3. measuring the diameters of the boles of all of the sample trees at regular intervals over their entire lengths and recording the data produced thereby;
4. measuring the green density of all of the sample trees at regular intervals over their entire lengths and recording the data produced thereby;
5. performing said density measuring step 4 using relatively long thin cores bored transverse to the axis of the tree;
6. transforming the height data of step 1 for all of the trees from actual units to a ratio of relative heights above a common reference plane;
7. transforming the diameter data of steps 1 and 3 for all of the trees from actual units to a ratio of relative diameters based on diameters inside and outside the bark;
8. correlating the relative diameter data of step 7 to the relative height data of step 6 and correlating the relative diameter data of step 7 to the green density data of step 4;
9. preparing tables and/or curves of the data resulting from steps 1, 3, 4, 6, 7 and 8;
10. determining the volumes of all the trees in the stand using the diameter data produced in step 3 and the classification data produced in step 1 together with the tables and/or curves produced in step 9 and volume equations applicable to the butt, middle and crown sections of the boles; and
11. determining the weights of all of the trees in the stand using the results of steps 9 and 10 above.

8. The method of claim 7, wherein the selected sample trees only are felled after step 2 and before step 3 to facilitate performing steps 3, 4 and 5.

9. The method of claim 7, wherein the cores used in steps 4 and 5 are bored to have a predetermined diameter, and the steps of curring said cores to a predetermined length, whereby said cut cores haves a predetermined volume, and cutting said cores to said predetermined length in such a way that said cut cores correctly simulate the ratio of sapwood to heartwood for each location along the length of the tree at which each core was bored in step 4.

10. The method of claim 7, and performing all of said step 3 to 11 inclusive in the field, on-site, in real time using only conventional forestry tools, a hand held programmable calculator or a small computer, and the data produced in step 1.

11. Apparatus for estimating the weight of the logs cut from a living stand of trees before the stand is harvested comprising a sample chamber and quill assembly, a tubular float chamber formed of transparent material to received said sample chamber and quill assembly, said sample chamber being of predetermined dimensions to receive a core bored out of a tree of predetermined length and predetermined volume therein, means to selectively seal said sample chamber, indicia on said quill corresponding to the weight and the density of said cores in said sample chamber when said sample chamber is floating in water, a predetermined amount of water in said chamber, said sample chamber and quill assembly being so calibrated when floating in water that the meniscus of the water on said quill will occur on said indicia so as to indicate the weight of a core in said floating sample chamber, and a scale having a predetermined length corresponding to the predetermined length of said sample chamber for cutting said cores to said scale's predetermined length, indicia on said scale to permit the cores cut thereon to said predetermined length to have a sapwood to heartwood ratio substantially equal to the sapwood to heartwood ratio of the tree at the location along the length of the tree at which the core was bored, said cores being bored out of said tree transverse to the axis of said tree and at regular intervals along the length of the said tree, and means to use the data produced by said instrument concerning all of said samples made from said cores bored at said regular intervals out of said tree to determine the weight of said tree and the weight of the logs to be cut from said tree.

12. The apparatus of claim 11, and a storage chamber, means to join said storage chamber to said float chamber in side-by-side relationship, removable plug means for said float chamber and for said storage chamber, spring shock absorber means in said storage chamber; and the lengths of said storage chamber, said plug means, said spring shock absorber means, and said sample chamber and quill assembly being such as to resiliently hold said sample chamber and quill assembly substantially immobile in said storage chamber when said plug means are secured thereto.

13. The apparatus of claim 12, wherein said float chamber and storage chamber plug means are interchangeable.

* * * * *